(12) United States Patent
Jarvik

(10) Patent No.: US 7,762,941 B2
(45) Date of Patent: Jul. 27, 2010

(54) BLOOD PUMP BEARINGS WITH SEPARATED CONTACT SURFACES

(75) Inventor: Robert Jarvik, Jarvik Heart Inc., 333 W. 52nd St., New York, NY (US) 10019

(73) Assignee: Robert Jarvik, New York, NY (US)

( * ) Notice: Subject to any disclaimer, the term of this patent is extended or adjusted under 35 U.S.C. 154(b) by 710 days.

(21) Appl. No.: 11/790,454

(22) Filed: Apr. 25, 2007

(65) Prior Publication Data
US 2008/0269880 A1 Oct. 30, 2008

(51) Int. Cl.
*A61N 1/362* (2006.01)
(52) U.S. Cl. ..................................... 600/16
(58) Field of Classification Search ............. 417/423.1; 600/16; 604/131
See application file for complete search history.

(56) References Cited

U.S. PATENT DOCUMENTS

| | | | |
|---|---|---|---|
| 4,994,078 A | 2/1991 | Jarvik | |
| 5,211,546 A | 5/1993 | Isaacson | |
| 5,613,935 A * | 3/1997 | Jarvik | ........................ 600/16 |
| 5,692,882 A | 12/1997 | Bozeman, Jr. et al. | |
| 5,947,892 A | 9/1999 | Benkowski | |
| 6,093,001 A | 7/2000 | Burgreen | |
| 6,761,532 B2 | 7/2004 | Capone et al. | |

* cited by examiner

*Primary Examiner*—George Manuel
*Assistant Examiner*—Robert N Wieland
(74) *Attorney, Agent, or Firm*—Troutman Sanders LLP

(57) ABSTRACT

Rotary hydrodynamic blood pumps have been used to treat over a thousand patients. The Jarvik 2000 has supported a patient for seven years and uses blood immersed bearings washed by high flow to avoid excessive thrombus formation. This permits the pump to be very simple and small. Nonetheless, the present Jarvik 2000 bearings and all other mechanical blood immersed bearings of the prior art have a supporting structure that predisposes to thrombus adjacent to the bearings. The present invention provides a bearing structure that eliminates this predilection site for thrombus formation, and may provide indefinite thrombus free operation. The rotor of the preferred embodiment includes a tapered hub fabricated of wear resistant material supported by three posts at each end of the rotor, upon which the rotor rotates. Blood washes the unobstructed spaces between the posts to prevent the accumulation of a torus of thrombus that could enlarge excessively.

23 Claims, 4 Drawing Sheets

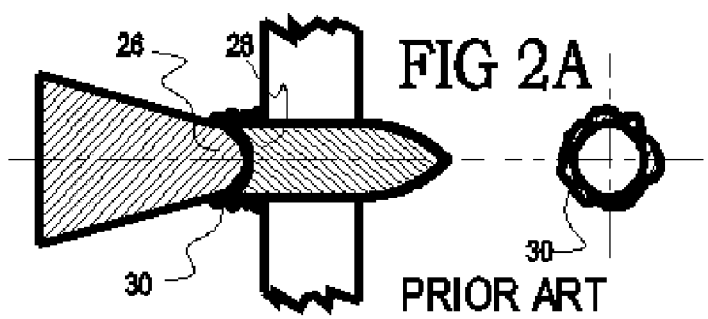
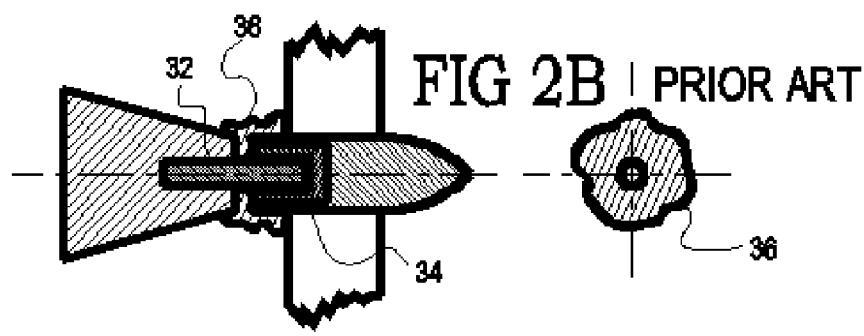
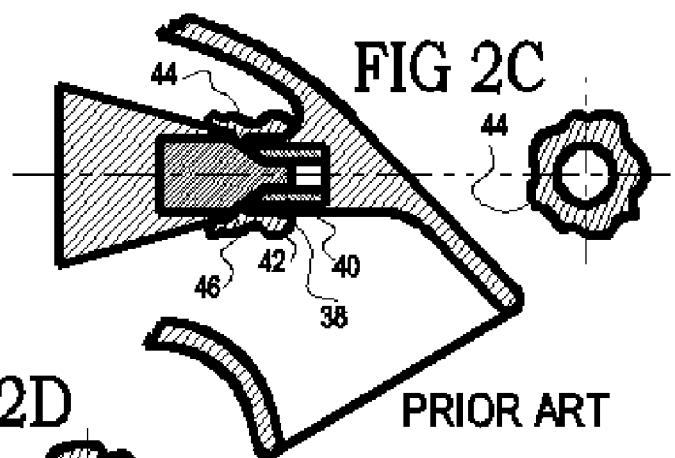
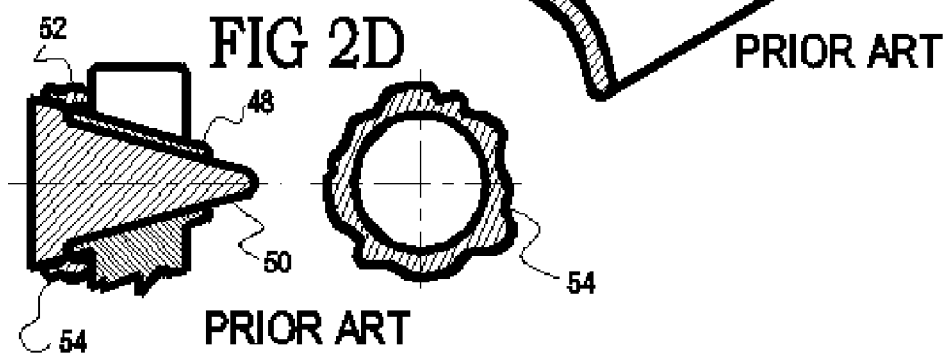

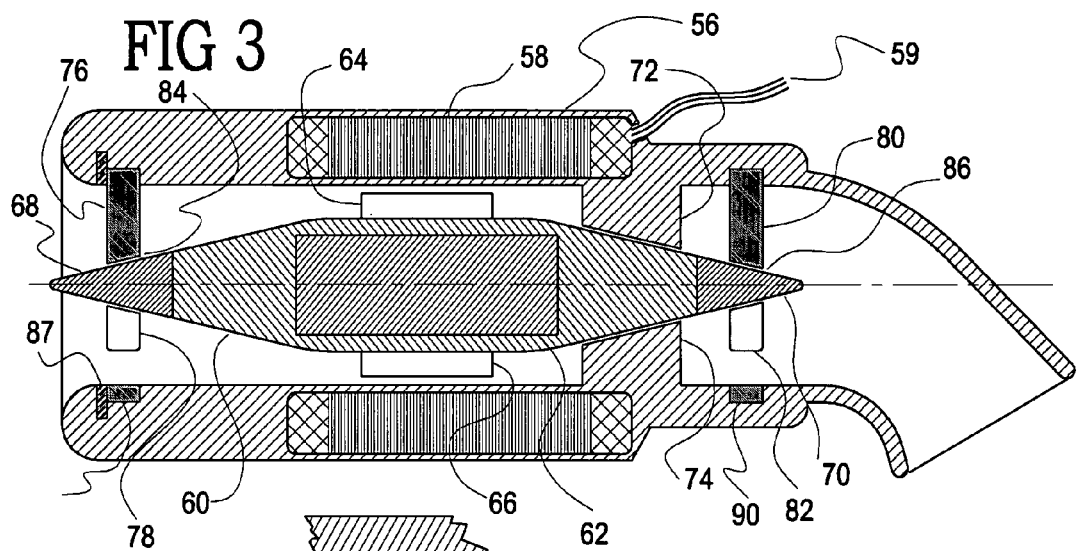
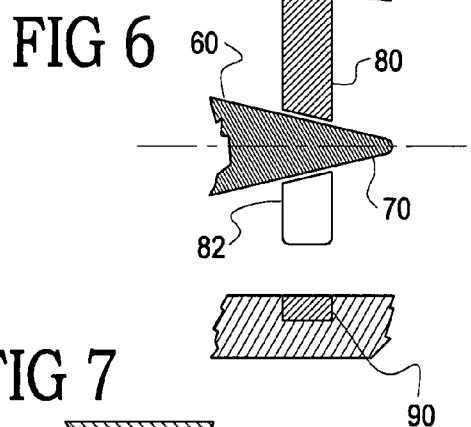
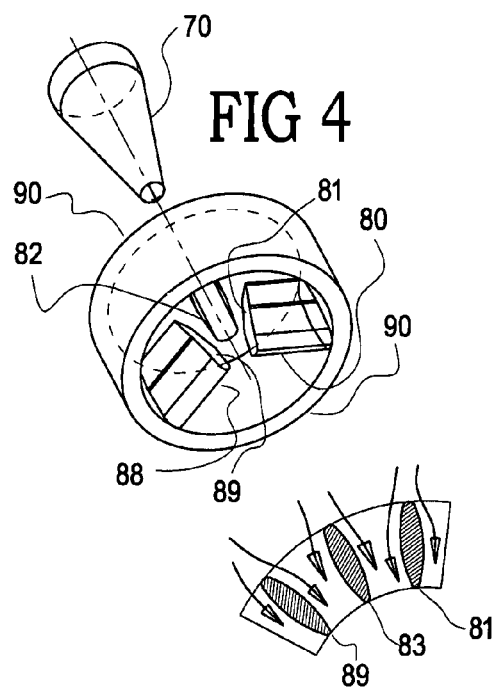
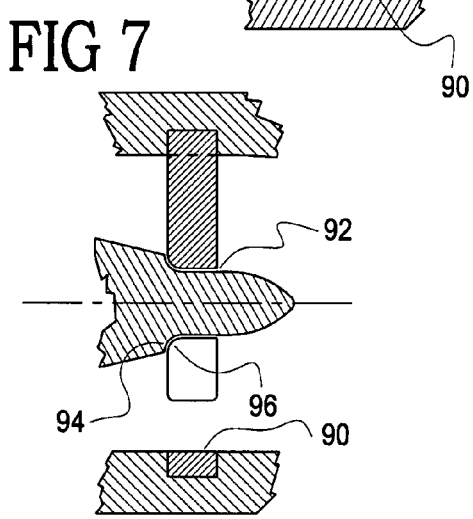

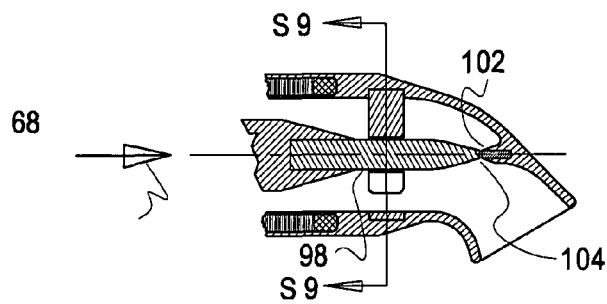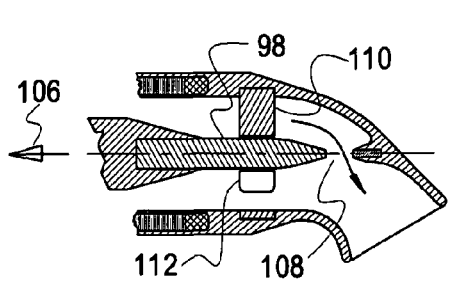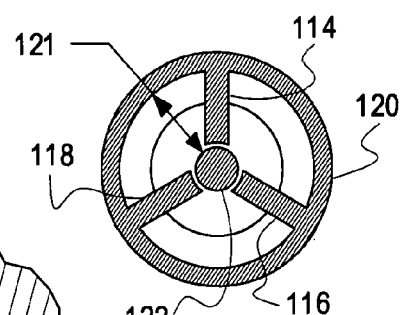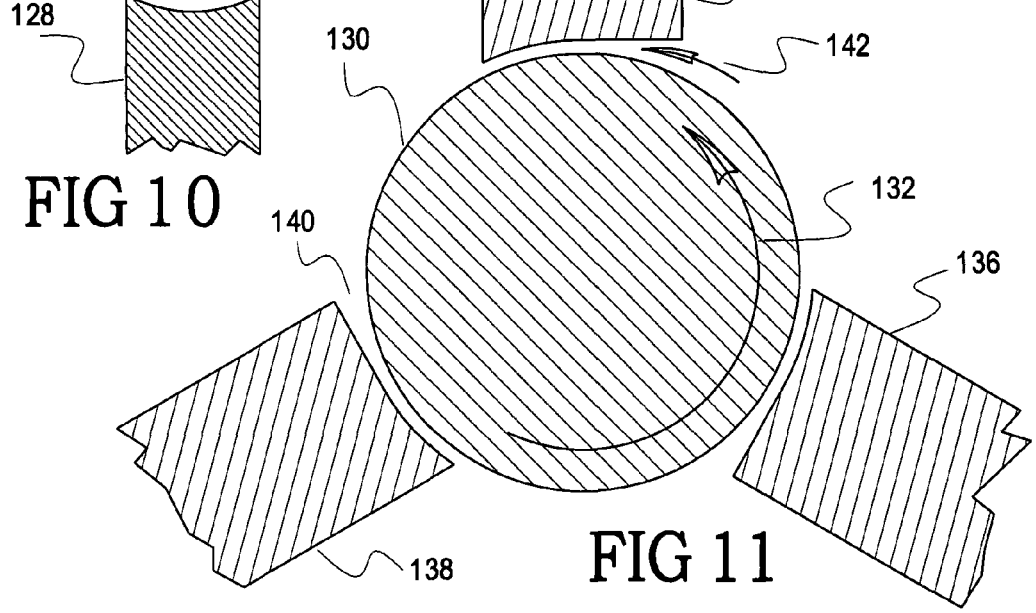

BLOOD PUMP BEARINGS WITH SEPARATED CONTACT SURFACES

BACKGROUND OF THE INVENTION

Over the past decade the use of rotary hydrodynamic blood pumps for both short term and long term circulatory support has expanded. The longest survival by any patient with a single heart assist device at the time of this application is seven years and ongoing utilizing a Jarvik 2000 axial flow left ventricular assist device with blood immersed ceramic bearings. In more than 200 cases using the Jarvik 2000 heart no mechanical bearing has ever failed due to wear or fatigue fracture. Other models of ventricular assist devices utilizing blood immersed ceramic bearings have also proven durable, such as the HeartMate II VAD, which is largely patterned after the Jarvik 2000. Computer analysis of the Jarvik 2000 bearing design supports the expectation that durability of 10-20 years or more is likely to be achieved.

In any rotating pump, a spinning impeller imparts hydrodynamic energy to the fluid. All rotational pumps must contain three elements, a housing which contains the fluid, a rotor which spins within the housing and imparts energy to the fluid, and a bearing system which supports the rotor, permitting rotation. Additionally, pumps require means to transmit torque to the rotor, which may be via a sealed shaft, or by magnetic forces.

Rotary blood pumps using a wide variety elements to achieve these requirements have been disclosed, and the rotary blood pump prior art now includes hundreds of patents. Generally, three types of bearing mechanisms are employed, 1) mechanical bearings, using fluid film lubrication or hydrodynamic fluid support, 2) fluid levitation, and 3) magnetic levitation. Also, various combinations of these are employed for thrust and radial support.

The present invention deals principally with mechanical blood immersed bearings in which fluid film lubrication is employed to support the radial bearing load, and complete, or partial magnetic thrust load support may additionally be provided.

In addition to providing a highly reliable and durable means of supporting the rotor, bearing systems for blood pumps must be hemo-compatible causing little blood damage or thrombus formation. In the case of mechanical bearings, this is generally accomplished by high flow washing of the junction of the rotating and stationary parts of the bearings as claimed in my early U.S. patent (Jarvik—U.S. Pat. No. 4,994,078). The present invention is an improvement over '078, providing an important new structure to achieve better blood flow washing of the bearings.

Usually axial flow blood pumps incorporating mechanical bearings use a tapered rotor having larger diameter in its center and tapered to a small diameter at each end. This permits small diameter bearings to be used, which is advantageous because the friction at the bearing surfaces is reduced compared to larger diameter bearings; this limits wear, power consumption by the bearing, and heat generation. Examples from the prior art include small ball in cup bearings, Burgreen—U.S. Pat. No. 6,093,001), jewel bearings with an olive and endstone, (Benkowski—U.S. Pat. No. 5,947,892), sleeve bearings with conical thrust bearing surfaces (Jarvik—U.S. Pat. No. 5,613,935) or with flat thrust bearing surfaces (Bozeman—U.S. Pat. No. 5,692,882), and grooved conical hydrodynamic bearings (Carrier—Pub No. 2007/0004959) adapted to carry both thrust and radial loads.

Another approach to mechanical blood immersed bearings disclosed in the prior art is lubricated support on the tips of pump impeller blades, or on shrouds surrounding impeller blades as disclosed by Shambaugh in U.S. Patent Application Publication No. 2007/0078293, which discloses a rotor supported on wide blade tips having a cylindrical portion and a tapered portion to support thrust loads. In U.S. Pat. No. 5,211,546 FIG. 7A, Isaacson disclosed an impeller hydro-dynamically supported on a shroud supported on the tips of the impeller blades. Both of these configurations have the disadvantage that the viscous friction in the gap between the rotating impellors and stationary housing is high, since the rotational velocity of the blade tips or shroud is maximum at the tip diameter.

Blood pumps using full magnetic levitation can be designed such that the dimension of the gaps between the magnetically levitated rotor and the stationary housing is large enough that blood damage or power losses due to shear in the gaps is negligible. The disadvantage of fully magnetically levitated blood pumps is that they are relatively large and complex compared to miniature pumps using mechanical bearings. In addition to the larger size and weight, they require active electromagnetic feedback control to maintain stability of the rotor, and this presents reliability issues with the electronics. If magnetic support is lost, the rotor will "crash" into the housing or stator blades, which could cause damage. Antaki, U.S. Pat. No. 6,761,532 provides wear resistant coatings on the blade tips, rotor hub, and housings of magnetically levitated blood pumps to reduce or eliminate damage in the event of failure of the magnetic support system. In FIG. 1, Antiki shows a structure where a tapered portion of the rotor hub, 38 can contact the tips of stator blades, 36, if the magnetic bearing system fails. The structure shown appears similar to some embodiments of the present invention, but would not provide a stable bearing system for the rotor, because the rotor would tilt from its usual rotational axis within the housing, and is not axially constrained.

In the bearing system of the present invention, the rotor of a hydrodynamic blood pump is rotationally supported on mating portions of the tips of support blades which contact its hub close to the center of rotation, and is axially restrained to prevent disengagement of the proper mating position of the rotating bearing surface in relation to the stationary bearing surfaces. In the preferred embodiment, two opposing bearings at each end of the rotor, limit axial and radial motion to as little as 50 millionths of an inch, while providing completely unconstrained rotational freedom.

The most important aspect of the present invention involves the pattern of washing of the bearings, by blood flow across them, to prevent thrombus. All other blood immersed mechanical bearing designs, except those that support the rotor on the impeller blade tips, (which has disadvantages described above) present a complete circumferential ring of bearing material to the bloodstream. This is an area of local flow stasis. Some thrombus tends to form on the surface. This then forms a continuous circumferential ring of thrombus surrounding the rotor adjacent to the junction of the rotating and stationary parts of the bearing. If high enough flow is provided across this area of the pump, the ring of thrombus may remain limited, in the form of a thin torus, and not become sufficiently large to interfere with the function of the pump. But if the material becomes infected, or if the flow is reduced to too low a level, or if the patient is hypercoagulable, the amount of thrombus may increase. The present invention eliminates any continuous ring of bearing material which can support growth of a torus of thrombus as described, while limiting the circumferential relative speeds of the bearing surfaces to the lowest practical values (because the bearing diameter is much less than the pump impeller tip diameter. This represents a major improvement over other blood immersed bearing designs.

A portion of the rotor surface having a small diameter relative to the impeller tip diameter is made of hard wear resistant material, and is circular on cross section at any point perpendicular to its axis of rotation. This surface may be cylindrical, conical, or another shape. The tips of two or more support posts, placed at generally uniform spacing around the circumference of the rotor and having mating surfaces in rotational contact with the bearing surface on the rotor, prevent the rotor from moving radially away from its axis of rotation. The contacting surfaces on the ends of the support posts constitute bearing "pads" upon which the bearing rotates. In the preferred embodiment there are two sets of these support posts, near each end of the rotor, and the bearing pads are tapered so that they act as both radial and thrust support members. The support posts are elongated and streamlined, and have the appearance of short blades. In a configuration with three such support blades at each end of the rotor, the spaces at the surface of the rotor between the blades are freely washed by generally axial flow proceeding through the pump.

Thus, in this region, formation of a torus of thrombus, which could enlarge and lead to problems, is avoided. A blood pump using this type of bearing can be designed to remain entirely free of thrombus accumulation throughout, as a fully magnetically levitated pump can also be. But the pump using the mechanical bearings of the present invention can be much simpler and much smaller.

OBJECTS OF THE INVENTION

1. It is an object of the present invention to provide a blood immersed bearing which has no "dead end" pocket in which thrombus can begin.

2. It is another object of the invention to provide mechanical bearings for rotary blood pumps that remain free of thrombus formation indefinitely.

3. It is another object of the present invention to provide mechanical bearings that are lubricated by a fluid film derived from blood and are fabricated from blood compatible wear resistant materials able to function properly for more than a decade, even without complete hydrodynamic fluid film support.

4. It is a further object of the present invention to provide an extremely space efficient blood pump bearing system to permit miniaturization of an entire axial flow VAD to less than 10 mm diameter by 2 centimeters long; small enough to be implanted into the non-coronary cusp of the aortic valve.

5. An additional object of the invention is to provide a miniature rotary blood pump bearing suitable for use with minimal or no anticoagulation.

THE DRAWINGS

FIG. 1 shows four longitudinal section drawings of generalized axial flow pumps from the prior art having four types of blood immersed bearing designs.

FIG. 1A represents a prior art pump having spherical surface bearings similar to U.S. Pat. No. 6,093,001.

FIG. 1B represents a prior art pump having pin in sleeve radial bearings with flat thrust bearing surfaces on the tip of the pins similar to U.S. Pat. No. 5,692,882.

FIG. 1C represents a prior art pump having pin in sleeve radial bearings surface bearings with tapered thrust bearing surfaces also supporting part of the radial load similar to U.S. Pat. No. 5,613,935.

FIG. 2 shows four enlarged detail longitudinal section drawings of the outflow side bearing of each of the pumps shown in FIG. 1, indicating the surfaces of the structure adjacent to the junction of the rotating and stationary parts which forms a circumferentially continuous surface on which a torus of thrombus can form.

FIG. 2A shows a sectioned view of the torus of thrombus on a spherical cup bearing.

FIG. 2B shows a sectioned view of the torus of thrombus on pin in sleeve bearing with a flat thrust bearing surface.

FIG. 2C shows a sectioned view of the torus of thrombus on a pin in sleeve bearing with a conical thrust bearing surface.

FIG. 2D shows a sectioned view of the torus of thrombus on a conical hydrodynamic bearing.

FIG. 3 is a longitudinal section view of an axial flow blood pump of the preferred embodiment incorporating the bearing structure of the present invention.

FIG. 4 is a perspective view of the bearing structure of the present invention at one end of the pump rotor, showing a conical portion of the rotor hub and three streamlined support posts making contact with the rotor.

FIG. 5 is a diagram of the conical bearing surface of the rotor, "unrolled" to represent the full 360 degrees of the surface. The shape of the three support posts are shown with arrows indicating flow washing around the posts.

FIG. 6 is a longitudinal section drawing of the bearing components and tapered end of the rotor from the preferred embodiment.

FIG. 7 is a longitudinal section of an embodiment of the invention having a cylindrical rotor hub in contact with the support posts, and having a step with a rounded shape, and corresponding rounded shape on the edge of the support posts to bear thrust load.

FIGS. 8A and 8B show two positions of another embodiment of the invention incorporating magnetic thrust load bearings combined with radial load bearing on the pads of support posts.

FIG. 9 is a view of the pump shown in FIG. 8A sectioned indicated S9 in FIG. 8A. This shows three support struts formed integral with an outer support ring, as is used in the preferred embodiment of FIG. 3 also shown "exploded" in FIG. 4.

FIG. 10 is a cross sectional view of an embodiment utilizing only two support posts, showing the circular section of a rotor and the two posts.

FIG. 11 is a cross section view of a configuration having a tapered portion of the bearing pad at the end of each post.

SPECIFIC DESCRIPTION OF THE INVENTION

Figure 1A:
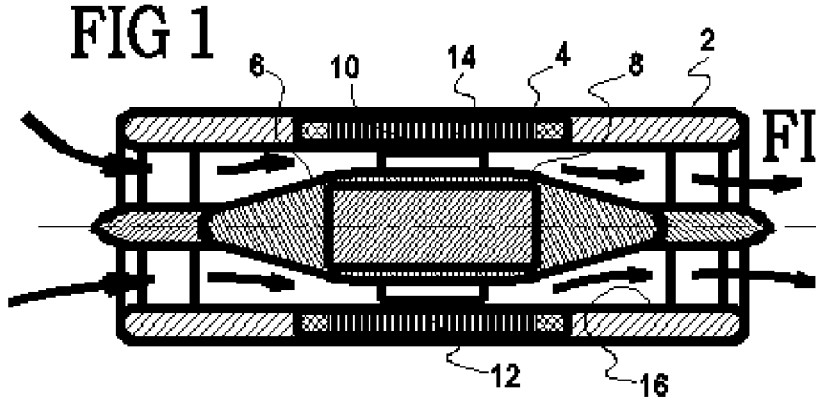
FIG. 1D represents a prior art pump having conical sleeve bearings with hydrodynamic taper and land features to support both radial and thrust load similar to U.S. Patent Application Publication No. 2007/0004959.
Figure 1B:
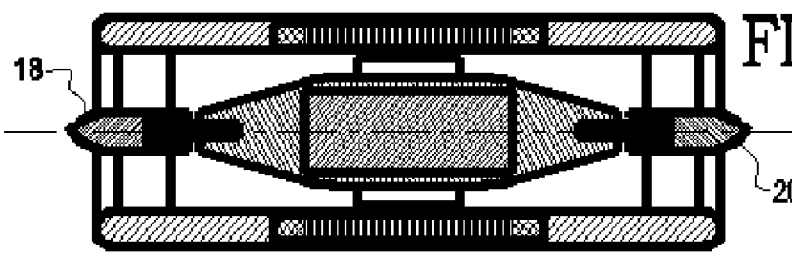
Figure 1C:
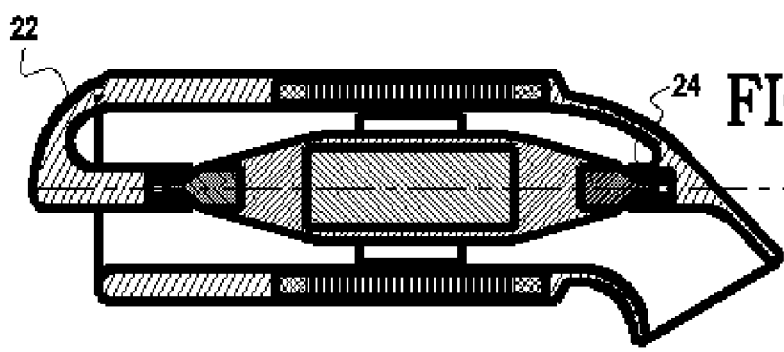
Figure 1D:
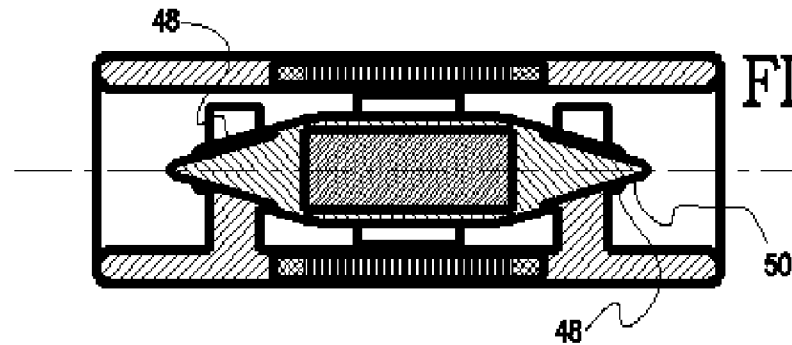

This invention comprises a specific type of blood immersed bearing suitable to carry the radial loads of a rotary blood pump rotor as well as the thrust loads. Depending on the details of each individual blood pump design utilizing this type of bearings, the bearing surfaces may be in mechanical sliding contact with mixed film lubrication or may achieve full hydrodynamic support with no mechanical contact of the rotating and stationary parts. In general, the bearing components are fabricated of blood compatible hard wear resistant materials such as ceramics. Where the term "ceramic" is used in this specific description of the invention, it should be understood that a wide range of materials may be used such as pyrolytic carbon, titanium nitride, diamond, diamond like coating, hard corrosion resistant metals, such as inconel, and the like. In the preferred embodiment, the bearings are small in diameter compared to the maximum tip diameter of the pump impeller. This keeps the rotational speed low compared to the rotational speed of the impeller (necessary to generate enough flow and pressure), and minimizes friction, heat generation, and wear. Considering a typical adult size axial flow pump with an impeller tip diameter of 0.600" operating at 10,000 RPM, the impeller tip speed would be 26 ft/sec. If the maximum diameter of the surface of the post contacting the rotor taper were 0.1" the surface speed at the position of friction would be only 4.3 ft/sec. This illustrates the advantage of supporting a rotor on the tips of support posts close to the axis of rotation, compared to supporting an axial flow rotor and impeller on the outside of the impeller blades, as has been disclosed in the prior art.

The essence of the current invention involves support of the pump rotor on the tips of streamlined posts. The greatest advantage of this is that washing of the bearing structure is improved compared to the bearing designs of the prior art and this invention provides bearings with the potential to remain completely free of thrombus indefinitely. In contrast to this, the blood immersed bearing designs of presently disclosed axial flow pumps all have a continuous circumferential surface in the immediate vicinity of the junctions of the rotating and stationary parts at the bearings. In clinically used pumps of this type, this surface often forms a small accumulation of thrombus, which becomes a continuous ring or torus of thrombus surrounding the rotor tip or bearing shaft. Since the torus is captured around the rotor or bearing shaft, it is trapped and held in place, and it can become enlarged. Fibrin which forms the thrombus is a very adherent stranded material which becomes wrapped around the shaft if it is not prevented from adhering by high blood flow washing forces. The continuous circumferential surfaces of the prior art bearings may also be located in very small areas of flow stagnation or recirculation due to small crevices. Elimination of these features which predispose to thrombus formation, combined with maintenance of high flow across all of bearing surfaces is a significant advantage of the current invention.

FIGS. 1 and 2 illustrate the disadvantageous mechanical structures found in all prior art axial flow pumps with blood immersed bearings (exclusive of pumps supported on the outside of the impeller tips).

Referring to FIGS. 1A, 1B, 1C, and 1D, in each drawing the housing 2 of an axial flow blood pump is a generally tubular structure containing a motor stator 4 that rotates a pump rotor 6 by electromagnetic forces exerted on a permanent magnet 8 contained within the rotor 6. The rotor supports impeller blades, 10, 12 which typically operate with a small tip clearance gap 14 between the blades and the ID of the housing 16. As the rotor turns, blood is pumped from the inflow side to the outflow side of the pump, as indicated by the arrows. Usually, outflow stator blades are provided downstream of the impeller to convert rotational fluid momentum to pressure energy making the pump more efficient than if outflow stators are not provided. For simplicity, the outflow stators are omitted from FIG. 1 and FIG. 2, Stationary support members are provided to support the stationary components of the bearings at each end of the rotor. These may be hubs 18, 20, as shown in FIGS. 1A, B, & D, or may be other structures such as a cage 22 and wall of a curved flow channel 24 shown in FIG. 1C. Each set of blood immersed bearings includes rotating components affixed to the pump rotor, and stationary components centered about the axis of rotation of the rotor at each end, and attached by some means to the pump housing.

FIGS. 2A, B, C, & D are enlarged views of the outflow side the bearings of the pumps shown in FIGS. 1A, 1B, 1C, & 1D respectively. To the right of each longitudinal section view is an end view (not sectioned) of the way the torus of thrombus would appear if removed from the pump. In FIG. 2A, a ball and cup type of bearing is shown with the spherical surface on the rotor 26 engaging in the stationary cup 28. The periphery of both of these parts each extends 360 degrees circumferentially, and a torus of thrombus 30 can form as shown. FIG. 2B illustrates a pin in sleeve bearing design, with a small diameter pin 32, engaged into sleeve 34. A torus of thrombus 36 filling a crevice between the rotating and stationary components is illustrated. In FIG. 2C, a pin in sleeve bearing is shown, with a cylindrical pin portion, 38 which turns within a sleeve 40 and a tapered portion 42, which bears a combination of radial and thrust load. A torus of thrombus 44 also can form on this design, which like all four illustrate, has a complete circumferential surface adjacent to the load bearing surface 46. FIG. 2D shows a conical bearing sleeve surrounding a tapered portion 50 of the rotor. As in the other designs, a continuous circumferential surface 52 encourages formation of a torus of thrombus 54.

Referring to FIG. 3, the preferred embodiment includes the pump housing 56 containing a motor stator 58, motor power wires 59, a pump rotor 60, containing a motor magnet 62, impeller blades, 64, 66, and two tapered ceramic rotating bearing shafts, 68, 70. Hydrodynamic outflow stator blades are shown 72, 74, that extend inwardly from the ID of the pump housing. At each end of the rotor bearing support posts 76, 78, 80, 82, extend inward from the ID of the pump housing to contact the tapered rotor bearing shafts as illustrated at 84, 86. In this embodiment three support posts are used on each end of the housing, but because of the sectioned view, only two are seen and the contact with the rotor of only one on each end is seen. Thus, there are six posts total in the pump, three at each end of the rotor, although embodiments can be used with only two posts at an end of the rotor as shown in FIG. 10, where the posts 126, and 128 capture the rotor 124 if the fit between the parts is close. The support posts may be composed of ultra-hard ceramic material and fabricated integral with a ring which support all three streamlined posts. This is best seen in FIG. 4 where all three posts, 80, 82, 88 are formed integral with a support ring, 90, and is further shown in FIG. 9 which shows the support ring 120 formed integral with three support posts, 114, 116, 118, which hold tapered shaft 122 centered for rotation. A channel is defined bordered by posts 114, 118 a portion of the rotor tapered shaft 122, and a portion of the post support ring 120. This channel is unobstructed for its full radial length, shown by the arrows at 121. Along the axial length of the channel, it may be tapered, as in the configuration of FIG. 3, or un-tapered, as in the configuration of FIG. 8, but in any case, only the hub, sides of the support posts, and inner boundary of the support ring are present.

Referring to FIG. 3, a resilient washer 87 composed of a blood compatible material such as polyurethane, may optionally be used to provide a light axial preload against the bearing post surfaces and rotor shaft. In FIG. 3 the resilient washer exerts an axial load on support ring 90 that causes the surfaces of the tapered bearing shafts and posts to contact at both inflow and outflow ends of the pump provided the proper fit of all of the parts in the assembly is used. FIG. 5 is a diagram of the tapered surface of the the rotating ceramic bearing shaft, 70. The three crosshatched ovals represent the footprints 81, 83, 89, of the three streamlined support posts 80, 82, 88. The arrows indicate flow around each of these "footprints" illustrate that there is no continuous circumferential surface or crevice on the bearing support post structure where thrombus may form a torus. The tapered ceramic bearing shaft has a continuous smooth polished surface in the vicinity of the contact point of the support posts. FIG. 6 is an enlarged view of the ceramic bearing components further illustrating that there is no circumferential gap or crevice at the bearing and no circumferential structure to encourage a torus of thrombus to form; this is prevented by the optimal washing of blood at the surface of the tapered rotating ceramic bearing shaft between the contact positions of the support posts.

FIG. 7 shows an embodiment of the present invention that utilizes a cylindrical wear resistant rotating bearing shaft 92 having a small step 94, formed to mate with a radius on the end of the support posts 96, configured to bear thrust load.

FIGS. 8A and 8B illustrate a further embodiment of the present invention in which the radial bearing load is supported on a cylindrical surface 98 designed to permit axial motion of the rotor. The position of the rotor when the pump is stopped is shown in FIG. 8A. The rotor is not rigidly constrained from axial motion at both ends of the rotor. A magnetic force in the direction of arrow 100 is provided by an offset of the motor magnet and motor stator laminations (as in the configuration shown in FIG. 3), that pushes the rotor axially against a mechanical ceramic stop pin 102 such that it contacts on the end of the rotor shaft 104 when the pump is stopped. When the pump is running it generates a pressure force that is exerted by the fluid in the direction of arrow 106, moving the rotor in the same direction as indicated by arrow 106 such that a gap 108 opens between the end of the rotor shaft 104 and the end of the stop pin 102. This gap is very well washed by flow to prevent thrombus formation. If the magnetic force is in the proper range, as the pump operates it will be supported radially by the mechanical bearings, and the thrust load will be born entirely magnetically.

FIG. 11 illustrates an embodiment in which the tips of the support posts are shaped so as to increase the hydrodynamic forces supporting the rotor. The tips of the three support posts, 134, 136, and 138, have a contour which creates a tapered channel 142, that blood enters as it is drawn into the gap between the post and rotor by viscous fluid forces applied to the film of blood very near the surface of the rotor as it turns in the direction shown by the arrow 132. This structure, typical of surfaces in many hydrodynamic bearing designs improves lubrication and may provide full hydrodynamic fluid support in some embodiments of the present invention.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. A bearing adapted to support the rotor of a blood pump for rotation comprising two or more posts extending from the periphery of a flow channel through which blood passes towards the axis of rotation of said rotor, each of said posts:

a.) terminating in a discrete surface separated from the other posts by a flow channel extending from the hub of the rotor for the full radial extent of the posts, and b.) having a longitudinal profile matching the longitudinal profile of a surface of the rotor that contacts the end surfaces of each post;

such that the rotor is free to rotate while maintaining direct mechanical contact support or fluid film support between the posts and the rotor at the surface of each post adjacent to the rotor.

2. The bearing of claim 1 in which the posts and portion of the rotor in contact with the posts are composed of a hard wear resistant material, such as ceramic or titanium with a surface coating of ultra-hard material such as titanium nitride or diamond-like carbon.

3. The bearing of claim 1 in which the posts are formed integral with ring of material used to mount the posts into the blood pump.

4. The bearing of claim 1 combined with a second bearing of the same type to support the other end of the pump rotor.

5. The bearing of claim 1 in which said longitudinal profile is a straight line at an angle of approximately 10-25% to the axis of rotation of the rotor.

6. The bearing of claim 1 in which said longitudinal profile includes an arc.

7. The bearing of claim 1 in which said longitudinal profile includes a line parallel to the axis of rotation of the rotor and also includes an arc.

8. The bearing of claim 1 in which the diameter of the largest portion of the rotor which contacts the posts is less than one half of the tip diameter of the pump impeller blades.

9. The bearing of claim 1 in which the posts are elongated and streamlined.

10. The bearing of claim 1 in which the posts are elongated and curved to function as flow straighteners for the pump.

11. The bearing of claim 1 in which the surface on the end of each post is shaped to form a tapered fluid channel with a decreasing cross-sectional area in the direction of rotational flow between the rotor and the supporting surface of the post.

12. A blood immersed bearing comprised of two or more streamlined vanes extending inwardly from the wall of a housing of a blood pump through which blood flows and within which a pump rotor rotates, in which said vanes contact the rotor so as to support it for rotation about its axis and also partition the flow into at least two completely unobstructed flow channels.

13. The bearing of claim 12 in which the vanes and portion of the rotor in contact with the vanes are composed of a hard wear resistant material, such as ceramic or titanium with a surface coating of ultra-hard material such as titanium nitride or diamond-like carbon.

14. The bearing of claim 12 in which the vanes are formed integral with a ring of material used to mount the vanes into the blood pump.

15. The bearing of claim 12 in which the diameter of the largest portion of the rotor which contacts the vanes is less than one half of the tip diameter of the pump impeller blades.

16. The bearing of claim 12 in which the vanes are curved to function as flow straighteners for the pump.

17. The bearing of claim 12 in which the surface on the end of each vane is shaped to form a tapered fluid channel with a decreasing cross-sectional area in the direction of rotational flow between the rotor and the supporting surface of the vane.

18. A axial flow blood pump bearing system to support a rotor having two oppositely tapered hub surfaces and a pump impeller supported there between, said rotor constrained to permit only rotation by contact directly upon a plurality of separated rotor support posts each of which contacts one of said tapered surfaces of the rotor.

19. The bearing of claim 18 in which the support posts and portion of the rotor in contact with them are composed of a hard wear resistant material, such as ceramic or titanium with a surface coating of ultra-hard material such as titanium nitride or diamond-like carbon.

20. The bearing of claim 18 in which the support posts are formed integral with a ring of material used to mount them into the blood pump.

21. The bearing of claim 18 in which the diameter of the largest portion of the rotor which contacts the support posts is less than one half of the tip diameter of the pump impeller blades.

22. The bearing of claim 18 in which the support posts are elongated are curved to function as flow straighteners for the pump.

23. The bearing of claim 18 in which the surface on the end of each support post is shaped to form a tapered fluid channel with a decreasing cross-sectional area in the direction of rotational flow between the rotor and the supporting surface of the post.

* * * * *